US006120529A

United States Patent [19]
Hartge et al.

[11] Patent Number: 6,120,529
[45] Date of Patent: Sep. 19, 2000

[54] METHOD FOR HEATING A HORIZONTAL RESTING SURFACE FOR PERSONS AND IRRADIATION APPARATUS

[75] Inventors: Jörg Eduard Hartge, Gelnhausen; Walter Scheller, Maintal; Markus Steckhan, Oberursel; Stefan Greif, Fulda; Georg Czernin, Aschaffenburg, all of Germany

[73] Assignee: Heraeus Med. GmbH, Hanau, Germany

[21] Appl. No.: 08/802,030

[22] Filed: Feb. 18, 1997

[30] Foreign Application Priority Data

Mar. 22, 1996 [DE] Germany ............... 196 11 251

[51] Int. Cl.⁷ .................................. A61N 21/00

[52] U.S. Cl. .................. 607/88; 607/96; 607/90

[58] Field of Search .................. 607/88–89, 90, 607/96, 94; 604/19–21; 606/2–3, 9, 15

[56] References Cited

U.S. PATENT DOCUMENTS

| 3,609,335 | 9/1971 | Kelly | 240/1.4 |
| 4,867,175 | 9/1989 | Takase | 607/102 |
| 5,511,563 | 4/1996 | Diamond | 128/898 |
| 5,649,924 | 7/1997 | Everett et al. | 606/15 |
| 5,707,401 | 1/1998 | Talmore | 607/88 |

*Primary Examiner*—John P. Lacyk
*Assistant Examiner*—Ryan Carter
*Attorney, Agent, or Firm*—Fulbright & Jaworski, LLP

[57] ABSTRACT

To heat horizontal surfaces on which patients are placed after surgery, an irradiation apparatus with halogen lamps is provided, the radiation of which is directed toward the horizontal surface to heat it. The surface temperature prevailing in the irradiated area of the horizontal resting surface is detected by a pyrometric sensor as long-wave infrared radiation. This temperature value is used as the controlled variable and is compared with a predetermined nominal value, such as 37° C. In the event of a deviation, a control signal corrects the irradiation intensity by adjusting the power supply to the halogen lamps.

9 Claims, 1 Drawing Sheet

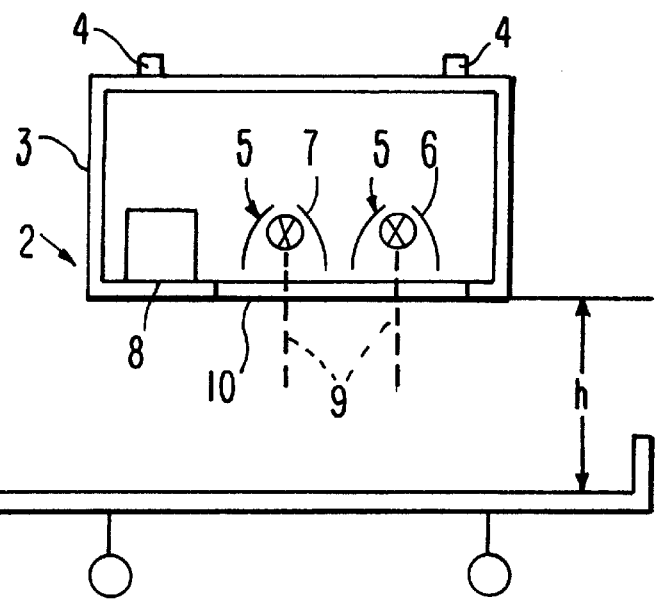
FIG.I
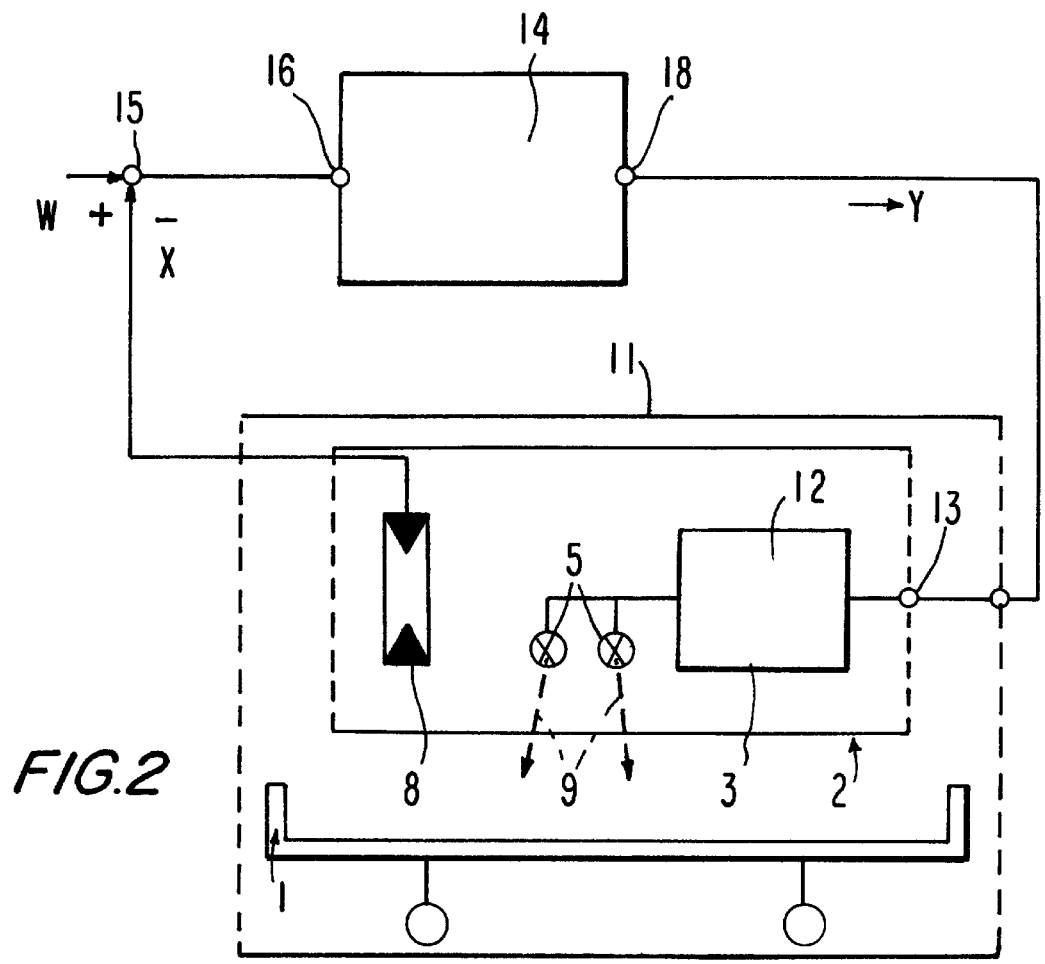
FIG.2

METHOD FOR HEATING A HORIZONTAL RESTING SURFACE FOR PERSONS AND IRRADIATION APPARATUS

BACKGROUND OF THE INVENTION

The invention pertains to a method for heating a horizontal resting surface for persons, especially for patients in a hospital, where the horizontal resting surface is irradiated by at least one radiation source mounted a certain distance away, and to an irradiation apparatus.

An irradiation apparatus for supplying heat continuously to a horizontal surface on which a person is resting is known from EP 254 838 B1. For this purpose, small-area heat radiators are provided, which are set up a certain distance above the corner points of a polygon surrounding the horizontal resting area.

It has been found to be a problem that, to mark out the radiation area, additional beams of light must be used to actually see where the irradiation area is; in addition, the heat absorption is subject to significant external interference, such as, for example, voltage fluctuations in the power supply of the radiator, variable ambient temperatures, and irregularities in the heat exchange between the irradiated surface and the environment.

An irradiation apparatus such as this, furthermore, is not at all suitable for preheating horizontal resting surfaces in the form of beds for patients, because the known irradiation apparatus is intended for the continuous irradiation of patients or infants, and no provisions are made to make it easy to replace one horizontal resting surface with another under the irradiation apparatus.

An electric light bath for treating areas of the human body with heat is also known from EP 275 817 B1; this apparatus includes at least one infrared source; radiation primarily in the wavelength range of 716–1,300 nm is produced by the radiation element. Rod-shaped infrared radiator elements are installed in a housing provided with reflectors, and a glass envelope and/or filter assembly is provided to reduce the amount of visible light. During use, it is possible to individually adjust the irradiation intensity by means of a control unit.

Because of the multiple reflectors in the beam outlet area, an apparatus of this type is not really suitable for heating the horizontal surfaces of hospital beds, because, first, the caregivers would perceive the reflectors as difficult to position, and, second, because it would also be necessary to deal with radiators of relatively large dimensions but without much ability to focus the rays.

SUMMARY OF THE INVENTION

The task of the invention is to preheat a horizontal surface on which the person can rest, without any attempt being made to irradiate the person either directly or indirectly; in particular, the task is to preheat hospital beds previously used by patients and onto which the patients are to be placed again after they have undergone a serious operation, the goal being to prevent the circulatory difficulties which can be caused by the drop in temperature which occurs in a conventional bed. In addition, high hygienic requirements are also to be satisfied, it being a particular goal to prevent the transfer of pathogens from one patient bed to another. The smoothest possible surfaces are to be used, furthermore, to ensure that the apparatus can be cleaned relatively easily.

The task is accomplished by irradiating the resting surface with radiation consisting essentially of wavelengths below 2500 nm, which can be provided by a halogen lamp and a reflector installed in a housing above the resting surface. The temperature of the surface is measured by detecting long (10 $\mu$m) wavelength radiation emitted by the surface. This temperature represents the controlled variable, which is compared to a nominal value, such as body temperature. The deviation is used to control the power supply for the lamp, so that the controlled variable conforms to the nominal value.

It is especially advantageous for the irradiation intensity to be controlled by a sensor, which detects the radiation emanating from the horizontal resting surface and sends the measured temperature value to the input of a controller. The preheating is thus able to meet high hygienic requirements. In addition, it is also possible to minimize external sources of interference, which is advantageous.

In a preferred embodiment of the irradiation apparatus, a halogen lamp is used as the heat radiator, the main radiation portion of which is in the spectral region below 2,500 nm, with a portion in the visible range of 400 to 700 nm.

A significant advantage is to be found in the possibility of covering the irradiation opening by means of a smooth-surfaced cover disk of thermally stable glass which is transparent to infrared radiation. It is possible to install the apparatus a relatively long distance, e.g., 1 m or more, away from the bed, which means that the apparatus can be mounted permanently on a bracket, such as on a bracket attached to the wall, at a height where it will be out of the way of the heads of the personnel.

Because of the pyrometric measurement, furthermore, it is also possible to smooth out temperature and voltage fluctuations and to adjust for different distances between the bed and the radiator assembly.

Because a radiation fraction is in the visible spectrum, the irradiated surface on the bed is clearly identifiable by the care personnel.

BRIEF DESCRIPTION OF THE DRAWING

FIG. 1 is a schematic longitudinal cross section through the irradiation assembly with the associated horizontal resting surface;

FIG. 2 is a schematic diagram of an associated feedback control system for adjusting the irradiation intensity.

DETAILED DESCRIPTION OF THE PREFERRED EMBODIMENT

According to FIG. 1, bed 1 is set up in the radiation area of an irradiation apparatus 2, where irradiation apparatus 2 and bed 1 are movable with respect to each other. In the present exemplary embodiment, irradiation device 2 is stationary, whereas bed 1 is mobile; it is advantageous for housing 3 of irradiation apparatus 2 to be mounted on a vertical wall by means of a bracket 4 above the head of the care-giver. In addition to radiators 5, shown schematically with halogen lamps 6 and reflectors 7, irradiation apparatus 2 also contains a pyrometric sensor 8, also shown schematically. Pyrometric sensor 8 is also located in housing 3 of irradiation apparatus 2 and is designed to receive the long-wave IR radiation (wavelength range, 6 to 16 $\mu$m, preferably about 10 $\mu$m) emanating from the horizontal resting surface as a result of its temperature; it has a thermopile, for example, as its detection element. A bolometer, however, can also be used. Irradiation axes 9 of radiators 5 are aimed at bed 1, axes 9 being illustrated only in symbolic fashion.

The bottom of irradiation housing 3 facing bed 1 is provided with a beam outlet disk 10 of thermally stable glass which is transparent to infrared radiation. Sensor 8 is also located on the bottom of irradiation housing 3 and is also aimed at the surface of bed 1.

The distance between the bottom of irradiation housing 3 and bed 1 is variable and is indicated in the drawing as "h".

Power is supplied to the irradiation apparatus by a permanent power grid. An additional emergency power supply unit may also be provided.

According to FIG. 2, irradiation apparatus 2 is designed as part of a control system 11, which includes irradiation housing 3, bed 1, sensor 8, and final control element 12 for the power supply to radiator 5. Radiators 5, the power supply unit, which receives a control signal y from controller 14 via input 13 and thus determines the intensity of the radiation directed to bed 1. Sensor 8 measures the surface temperature of bed 1 and sends this temperature value, determined in the form of long-wave radiation (thermal radiation), as controlled variable x to comparison point 15 at input 16 of controller 14; at the same time, the nominal value signal w for the desired temperature on the bed, e.g., a 37° C. signal for the body temperature, is also supplied to comparison point 15. The deviation (w−x) resulting from the difference between controlled variable x and nominal value w is sent to input 16 of controller 14, where it is converted into a control signal y which is made available at output 18 of controller 14. Control signal y is then sent to input 13 of final control element 12, which supplies power to radiators 5.

It has been found to be especially advantageous that any disturbances acting on final control element 12, such as fluctuations in the supply grid or variations in the ambient temperature, in the air flow, or in the distance between the irradiation apparatus and the bed, are detected as interference by the feedback control system, which can thus correct any deviations between the nominal and actual values by means of its control signals.

It has also been found to be advantageous that the irradiation apparatus makes it possible to see the irradiated surface. Thus the care-giving personnel are clearly informed where the preheated area of the horizontal resting surface is.

What is claimed is:

1. Method for heating a resting surface, said method comprising irradiating said surface with radiation consisting essentially of wavelengths below 2500 nm, detecting infrared radiation emanating from said surface,
   determining a temperature value based on said detected radiation,
   determining a deviation between said temperature value and a predetermined nominal value, and
   adjusting intensity of radiation irradiating said surface based on said deviation, wherein said radiation emanating from said surface is in the wavelength range of 6 to 16 $\mu$m and is detected by a sensor.

2. Method as in claim 1 wherein said surface is irradiated with radiation from a halogen lamp.

3. Method as in claim 1, wherein said radiation is produced by a heat radiator having a black body temperature in a range up to 3400°K.

4. Apparatus for heating a resting surface, for patients in a hospital, said apparatus comprising
   a heat radiator emitting radiation having an intensity toward said resting surface,
   a power supply for controlling the intensity of said radiation,
   a sensor which measures thermal radiation emitted by said surface, and
   a controller having an input connected to said sensor and an output connected to said power supply, wherein said heat radiator is provided for a radiation consisting essentially of wavelengths below 2500 nm and wherein said sensor is a pyrometer for measuring infrared radiation in the range of 6 to 16 $\mu$m.

5. Apparatus as in claim 4 wherein said heat radiator comprises a halogen lamp having radiation consisting essentially of wavelengths below 2500 nm.

6. Apparatus as in claim 5 further comprising
   a housing in which said lamp is located,
   a reflector located above said lamp in said housing, and
   a disk of thermally stable glass which is transparent to thermal radiation below said lamp, said disk being incorporated in said housing to seal off said lamp from said surface.

7. Apparatus as in claim 4, wherein said pyrometer is a thermopile.

8. Apparatus as in claim 4, wherein said pyrometer is a bolometer.

9. Apparatus as in claim 4, wherein said heat radiator has a black body temperature in a range up to 3400°K.

* * * * *